(12) United States Patent
Feng et al.

(10) Patent No.: US 11,234,598 B2
(45) Date of Patent: Feb. 1, 2022

(54) MAGNETIC RESONANCE ELASTOGRAPHY IMAGING METHOD AND BRAIN AND ABDOMEN REGION IMAGING ACTUATOR

(71) Applicants: Yuan Feng, Jiangsu (CN); Long Huang, Jiangsu (CN)

(72) Inventors: Yuan Feng, Jiangsu (CN); Long Huang, Jiangsu (CN)

(*) Notice: Subject to any disclaimer, the term of this patent is extended or adjusted under 35 U.S.C. 154(b) by 959 days.

(21) Appl. No.: 15/671,163

(22) Filed: Aug. 8, 2017

(65) Prior Publication Data
US 2018/0271376 A1 Sep. 27, 2018

(30) Foreign Application Priority Data

Mar. 23, 2017 (CN) .......................... 201710177765.6
May 10, 2017 (CN) .......................... 201710326020.1

(51) Int. Cl.
| | | |
|---|---|---|
| *A61B 5/00* | (2006.01) | |
| *A61B 5/055* | (2006.01) | |
| *A61B 8/08* | (2006.01) | |
| *G01R 33/563* | (2006.01) | |

(52) U.S. Cl.
CPC .......... *A61B 5/0051* (2013.01); *A61B 5/0042* (2013.01); *A61B 5/055* (2013.01); *A61B 8/485* (2013.01); *G01R 33/56358* (2013.01); *A61B 5/725* (2013.01); *A61B 5/7257* (2013.01)

(58) Field of Classification Search
CPC ..... A61B 5/0051; A61B 5/0042; A61B 5/055; A61B 8/485; A61B 5/725; A61B 5/7257; G01R 33/56358
See application file for complete search history.

(56) References Cited

U.S. PATENT DOCUMENTS

| | | | | |
|---|---|---|---|---|
| 5,952,828 | A * | 9/1999 | Rossman | A61B 5/055 324/318 |
| 8,305,076 | B2 * | 11/2012 | Sack | A61B 5/0051 324/309 |
| 2008/0251678 | A1 * | 10/2008 | Lien | F16M 11/10 248/404 |
| 2013/0239690 | A1 * | 9/2013 | Tadano | G01R 33/56358 73/644 |
| 2014/0291555 | A1 * | 10/2014 | Sakuragi | A61B 6/4405 250/493.1 |
| 2014/0330122 | A1 * | 11/2014 | Baghani | A61B 8/463 600/438 |

(Continued)

OTHER PUBLICATIONS

Tse et al. "Magnetic resonance elastography hardware design: a survey," J. Engineering in Medicine. vol. 223, 2009. p. 497-514 (Year: 2009).*

*Primary Examiner* — Catherine B Kuhlman
*Assistant Examiner* — Sean A Frith
(74) *Attorney, Agent, or Firm* — SZDC Law P.C.

(57) ABSTRACT

A device to estimate mechanical properties of brain and abdomen organs undergoing magnetic resonance elastography (MRE) includes electromagnetic actuators, mechanical wave generation mechanisms, and a control unit to generate oscillatory motion signals in synchronization with the MR scanner. Preserving only the shear wave component, a local fitting algorithm is used to estimate the viscoelastic properties of soft tissues. The device is portable and easy to implement in clinical diagnostics, and can be modified to measure other soft materials.

1 Claim, 8 Drawing Sheets

(56) References Cited

U.S. PATENT DOCUMENTS

2015/0366433 A1* 12/2015 Atarot .................. A61B 1/0016
　　　　　　　　　　　　　　　　　　　　　　600/102
2016/0007968 A1* 1/2016 Sinkus ................. A61B 5/0051
　　　　　　　　　　　　　　　　　　　　　　600/410

* cited by examiner

MAGNETIC RESONANCE ELASTOGRAPHY IMAGING METHOD AND BRAIN AND ABDOMEN REGION IMAGING ACTUATOR

BACKGROUND OF THE INVENTION

The present invention is in the field of medical imaging and diagnosis. Particularly, this is a magnetic resonance elastography method and imaging actuators for brain and abdomen region.

Magnetic resonance elastography is one of the clinically used diagnosis method based on the biomechanical properties of soft tissues. Magnetic resonance elastography has been used clinically in detecting liver fibrosis. Currently, the imaging actuators for brain tissue include (1) pneumatic actuation using pads filled with air; (2) rod actuation rigidly connected to the skull; (3) actuation using bite bar.

The pneumatic actuation method uses two soft pad filled with air for vibration induction. Two air tubes with relatively large diameters are used to connect the passive actuator pads in the scanner room and the control console. The whole assembly needs relatively large spaces for both the passive and active actuator. A large connection hole between the scanner and control room is needed for the air tubes. At the same time, the active actuator with an air pump needs large spaces and is not easy to move around.

The rod actuation method uses a long rigid rod to connect the actuation device with a skull holder. The skull holder is rigidly connected to the human skull and is placed inside the head coil. This actuator assembly encompasses a large space and the preparation time is long. The rigid rod and skull holder are difficult to install and hard to move around.

The bite bar actuation method is similar to aforementioned rod actuation. Instead, a bite bar is needed for patients to bite in order to transmit the vibration from the actuator to the brain. It is not convenient for the patient to carry out the tests and the preparation and set up procedure are also complicated.

Currently, the clinically used modulus estimation method for magnetic resonance elastography is based on the local wave frequency estimate and the wave propagation equation of linear elastic material. This method can estimate the elastic modulus of soft tissues, but not the viscoelastic properties. The method using finite element method requires accurate boundary condition settings, which is hard to set up and the computation efficiency is not clinically applicable.

The pneumatic actuation method is using an air pump to induce mechanical waves to soft tissues. The main disadvantages of the method are 1. The accuracy of the actuation frequency is hard to control; 2. Accessories include thick and long air tubes, air pump and controllers that require long set up time and are not suitable for limited clinical spaces; 3. The pneumatic actuation could induce noises and have a high requirement for airtight components.

BRIEF SUMMARY OF THE INVENTION

The purpose of the present invention is to solve the above problems of the prior art and to provide a magnetic resonance elastography method for measuring the brain and soft tissues in the abdomen region. The method is computationally efficient; the apparatus are easy to use and portable. The actuator receives signals from a signal generator, producing mechanical vibrations in the magnetic field. Both the actuator for brain and abdomen region has a compressing plate for inducing the mechanical waves into the tissue. The actuators have simple structures, easy to use, convenient to carry out measurements, portable, and noise-free. The actuators are suitable to use in any types of commercial magnetic resonance imaging systems.

The invention utilizes the following technical solutions:

Design (I)

A magnetic resonance elastography method for measuring the elastic properties of soft tissues, wherein the method contains the following steps:

① induce mechanical waves in soft tissues with a frequency of $\omega$;

② measure the phase of the image which corresponds to the wave displacement;

$$\vec{u} = \frac{\omega \vec{\varphi}}{\gamma \pi N G_0}$$

③ calculate displacement u(t) with respect to time using, where $\vec{u}$ is the displacement vector and $\vec{\omega}$ is the phase value.

④ apply Fast Fourier Transform to u(t), calculate the first principal component $U_1$.

⑤ apply spatial filtering to $U_1$, and calculate the curl value of the filtered $U_1$. In this way, only the shear wave component was kept.

⑥ use least square fitting to estimate the shear modulus at each pixel point, calculate the storage modulus G' and loss modulus G" to get a distribution map of the modulus of the soft tissue.

where $\omega$ is the vibration wave frequency, $\gamma$ is the gyroscopic ratio, G0 is the magnitude of the motion encoding gradient, N is the number of motion encoding cycles of applying the motion encoding gradient.

The displacement of the wave propagation $\vec{u}(t)$ in a linear elastic material satisfies $$\rho \frac{\partial^2 \vec{u}}{\partial t^2} = \mu \nabla^2 \vec{u} + (\lambda + \mu) \nabla (\nabla \cdot \vec{u}).$$

If considering only the shear wave propagation, the equation could be simplified as $$\rho \frac{\partial^2 \vec{u}}{\partial t^2} = \mu \nabla^2 \vec{u},$$

and in terms of $\omega$, $$-\rho \omega^2 U_1 = \mu \nabla^2 U_1,$$

where $\rho$ is the density of the soft tissue, $\mu$ is shear modulus, $\lambda$ is lame's constant.

Substitute $\mu$ and $U_1$ with complex variables $\mu=\mu'+i\mu''$ and $U_1=U_1'+iU_1''$ to get the equation of estimating shear modulus $\mu$ $$-\rho \omega^2 \begin{bmatrix} U_1' \\ U_1'' \end{bmatrix} = \begin{bmatrix} \nabla^2 U_1' & -\nabla^2 U_1'' \\ \nabla^2 U_1'' & \nabla^2 U_1' \end{bmatrix} \begin{bmatrix} \mu' \\ \mu'' \end{bmatrix}$$

where ρ is the density of the soft tissue, ω is the vibration frequency $U_1'$ is the first principal component of the filtered and curled $U_1$ value, $U_1''$ is the corresponding imaginary component, μ' is the storage modulus, μ" is the loss modulus.

The least square fitting method of step ⑥ is: calculate $U_1'$ and $U_1''$ values of each pixel point, then estimate the shear modulus p using a patch of pixels surrounding the target pixel, the fitting window size could be 3×3, 5×5, or 7×7.

The filtering algorithm in step ⑤ is selective based on the dimension of $\vec{u}(t)$. If $\vec{u}(t)$ is a 3D array, the mean filtering is applied; when $\vec{u}(t)$ is a 2D vector, ideal filter or Butterworth filter is applied.

Design (II)

A magnetic resonance elastography imaging apparatus for brain tissue, wherein the apparatus comprises the base placed on top of the head coil; two clamps for holding the base on top of head coil; a positioning adjustment slider that mounted on base, which can slide along the grooves of the base; a place locking mechanism I that can fix the position of slider on top of base; a vibration plate that connects to a supporting rod mounted on the slider, placed at the end of the supporting rod. Both the head coil and the base have open grooves for allowing motions of the supporting rod. The end of the supporting rod that connected to the vibration plate was placed inside of the head coil, in the open space of the head coil.

The aforementioned supporting rod comprises an upper part; a sliding hole is inside the upper part, a lower part that can slide inside the sliding hole, and a locking mechanism II that can fix the relative position between the upper part and lower part.

The aforementioned adjustment slider has a rotating shaft on top; the supporting rod is hinged to the rotating shaft. The axial direction of the rotating shaft is perpendicular to the adjustment slider.

The aforementioned clamps comprise two U-shaped plates that are arranged on both sides of the base and are connected between the magnetic resonance head coil and the base, two fixing bars screwed on each of the U-shaped plates respectively, and two compressing plates at the ends of the fixing bars. When in a compressed state, the compressing plates press on the upper surface of the base.

Compared with the current technology, the present invention designs (I) and (II) has the following advantages:

(1) The present invention offers a magnetic resonance elastography imaging method and apparatus, which is computationally efficient and can be widely implemented in the current magnetic resonance imaging scanner systems. The actuator takes the signals generated from the signal generator and induces vibration in the magnetic field. The pressing plate induces mechanical waves in the soft tissues through vibration, therefore implement the magnetic resonance elastography. The actuators have simple structures, easy to use, convenient to carry out measurements, portable, and noise-free. The actuators are suitable to use in any types of commercial magnetic resonance imaging systems;

(2) The actuator of the present invention for brain magnetic resonance elastography has a adjustable pressing plate, whose position can be adjusted relative to the base in either left-right, anterior-posterior, and foot-head directions, suitable for patients with different head dimensions.

(3) The actuator of the present invention for brain magnetic resonance elastography is easy to install, without any intervention of the human parts such as bite bar or skull fixing device. This greatly reduces the patient setup time, improves the patient care quality, and is cost efficient.

(4) The actuator of the present invention for brain magnetic resonance elastography utilizes mechanical actuation method; improve the frequency and magnitude control accuracy compared with that of the pneumatic actuator.

(5) The modulus estimating method can calculate both the storage and loss modulus of the soft tissue, providing a complete picture of the viscoelastic properties of the soft tissue.

Another purpose of the present invention is to provide an actuator for abdomen magnetic resonance elastography. The apparatus receives signals from a signal generator, induces vibration of a pressing plate in the magnetic field, and therefore produces magnetic resonance elastography imaging. The apparatus is easy to setup and use, portable and suitable for patients with different body size and weight.

Design (III)

An actuator for magnetic resonance elastography imaging of the abdomen region, wherein it comprises of a base, a lifting base that is placed on the base and can sliding relative to the base, a locking mechanism I placed between bases and lifting base for fixing the relative position of the base and lifting base, a mounting base that is installed on the side of the lifting base, a sliding base installed on the mounting base that can slide relative to the mounting base. A locking mechanism II installed between the mounting base and the sliding base for limiting the motion between the sliding base and the mounting base, and the supporting rod hinged on the sliding base. The actuator for magnetic resonance elastography imaging also includes a electromagnetic coil installed on the supporting rod that is closed to the mounting base, a compressing plate installed at the end of the supporting rod. The hinge axis of the supporting rod is perpendicular to the axis of the supporting rod, and close to the coil. The lifting base has curved grooves on top for placing the supporting rod.

Preferably, a rotating shaft is installed on top of the sliding base, and the supporting rod is hinged to the rotating shaft.

Preferably, the lifting base connects to the base via a sliding block module, the locking mechanism I are threaded bolts between the lifting base and base.

Preferably, the mounting base has two parallel sliding grooves, the sliding base has positioning block that matches the sliding grooves, the locking mechanism II are a threaded bolts between the mounting base and the sliding base.

Compared with the current technologies, the present invention design (III) has the following advantages.

(1) The actuator for magnetic resonance elastography imaging of the abdomen region can control the frequency and vibration magnitude precisely, easy to set up, easy to use, and portable. The actuator is adjustable for patients with different size and weight.

(2) The actuator for magnetic resonance elastography imaging of the abdomen region can adjust the position of the sliding base on the installation base to change the vibration motion magnitude and effectiveness.

(3) The actuator for magnetic resonance elastography imaging of the abdomen region is noise-free, cost effective, and easy to implement clinically.

Notations: 1. Head coil; 11. inner space of the head coil; 2. Base; 3. Pressing device; 31 U-shape plate; 32. Compressing rod; 33. Compressing plate; 4. Sliding base; 41. Rotating shaft; 5. Supporting rod; 51. Upper part of the supporting rod; 52 lower part of the supporting rod; 6. Coil; 7. Compressing plate; 1'. Base; 2'. Lifting base; 3'. Installation base; 31'. Sliding grooves; 4'. Sliding base; 41'. Rotating shaft; 5'. Supporting rod; 6'. Coil; 7'. Compressing plate.

DETAILED DESCRIPTION OF THE INVENTION

Description of the Preferred Embodiments

Embodiments (I)

A magnetic resonance elastography method for measuring the elastic properties of soft tissues, wherein the method contains the following steps:

① induce mechanical waves in soft tissues with a frequency of ω;

② measure the phase of the image which corresponds to the wave displacement;

③ calculate displacement u(t) with respect to time using, $$\vec{u} = \frac{\omega \vec{\varphi}}{\gamma \pi N G_0}$$

where $\vec{u}$ is the displacement vector and $\vec{\omega}$ is the phase value.

④ apply Fast Fourier Transform to u(t), calculate the first principal component $U_1$.

⑤ apply spatial filtering to $U_1$, and calculate the curl value of the filtered $U_1$. In this way, only the shear wave component was kept.

⑥ use least square fitting to estimate the shear modulus at each pixel point, calculate the storage modulus G' and loss modulus G" to get a distribution map of the modulus of the soft tissue.

where ω is the vibration wave frequency, γ is the gyroscopic ratio, $G_0$ is the magnitude of the motion encoding gradient, N is the number of motion encoding cycles of applying the motion encoding gradient.

The displacement of the wave propagation $\vec{u}(t)$ in a linear elastic material satisfies $$\rho \frac{\partial^2 \vec{u}}{\partial t^2} = \mu \nabla^2 \vec{u} + (\lambda + \mu) \nabla (\nabla \cdot \vec{u}).$$

If considering only the shear wave propagation, the equation could be simplified as $$\rho \frac{\partial^2 \vec{u}}{\partial t^2} = \mu \nabla^2 \vec{u},$$

and in terms of ω, $$-\rho \omega^2 U_1 = \mu \nabla^2 U_1,$$

where ρ is the density of the soft tissue, μ is shear modulus, λ is lame's constant.

Substitute μ and $U_1$ with complex variables μ=μ'+iμ" and $U_1=U_1'+iU_1"$ to get the equation of estimating shear modulus μ

$$-\rho \omega^2 \begin{bmatrix} U_1' \\ U_1'' \end{bmatrix} = \begin{bmatrix} \nabla^2 U_1' & -\nabla^2 U_1'' \\ \nabla^2 U_1'' & \nabla^2 U_1' \end{bmatrix} \begin{bmatrix} \mu' \\ \mu'' \end{bmatrix}$$

where ρ is the density of the soft tissue, ω is the vibration frequency, $U_1'$ is the first principal component of the filtered and curled $U_1$ value, $U_1"$ is the corresponding imaginary component, μ' is the storage modulus, μ" is the loss modulus.

The least square fitting method of step ⑥ is: calculate $U_1'$ and $U_1"$ values of each pixel point, then estimate the shear modulus μ using a patch of pixels surrounding the target pixel, the fitting window size could be 3×3, 5×5, or 7×7.

The filtering algorithm in step ⑤ is selective based on the dimension of $\vec{u}(t)$. If $\vec{u}(t)$ is a 3D array, the mean filtering is applied; when $\vec{u}(t)$ is a 2D vector, ideal filter or Butterworth filter is applied.

Figure 1:
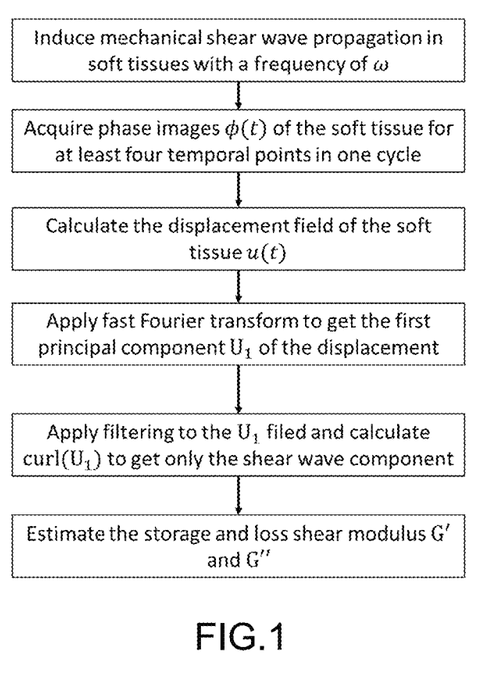
FIG. 1 is a flow chart of the procedure of the magnetic resonance elastography method of the present invention.
Figure 2:
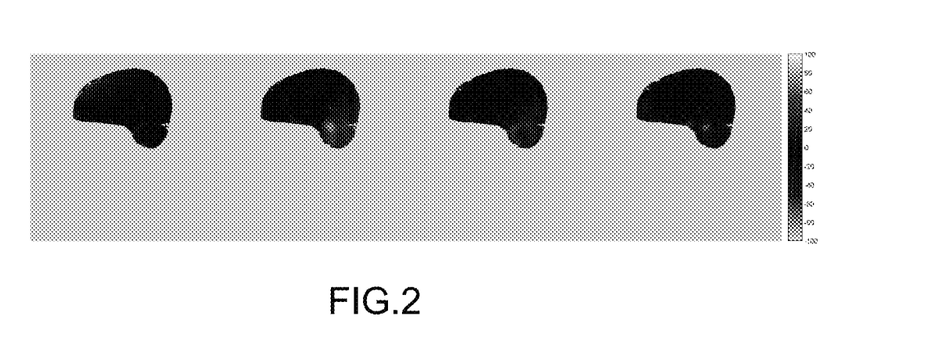
FIG. 2 is a displacement distribution map of the wave propagation inside brain tissue at a vibration frequency of 60 Hz (units in μm).
Figure 3:
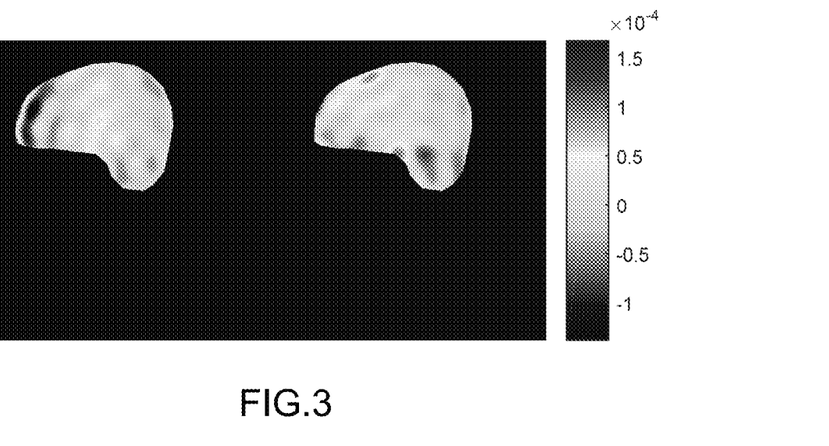
FIG. 3 is distribution maps of U1' (left) and U1" (right) from FIG. 2.
Figure 4:
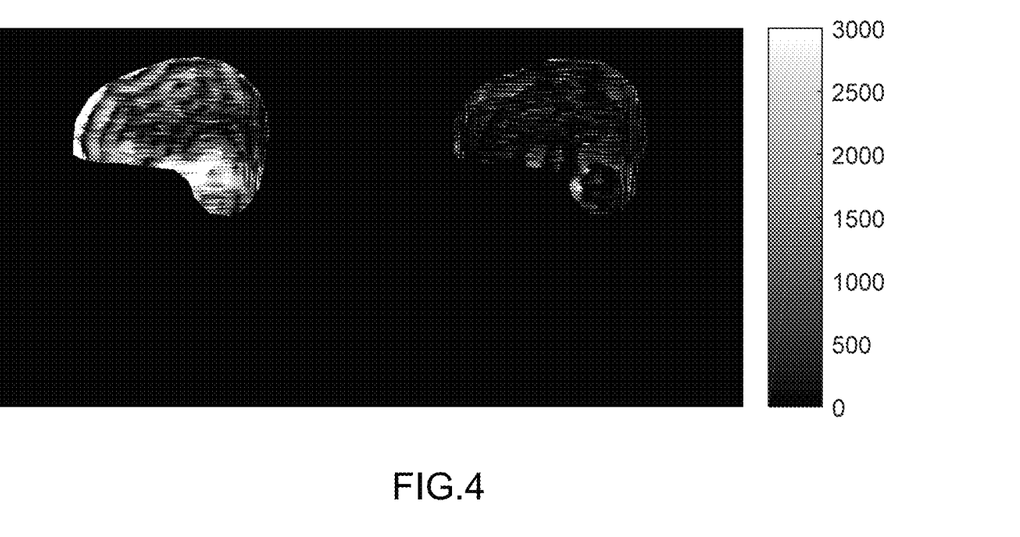
FIG. 4 is estimated G' (left) and G" (right) values using least square fitting based on the wave propagation equation from FIG. 3. (units in Pa)

Displacement of the wave propagation in brain tissue with an actuation frequency of 60 Hz is shown in FIG. 2. FIG. 3 is distribution maps of $U_1'$ (left) and $U_1"$ (right) from FIG. 2. FIG. 4 is estimated G' (left) and G" (right) values using least square fitting based on the wave propagation equation from FIG. 3.

Embodiments (II)

Figure 5:
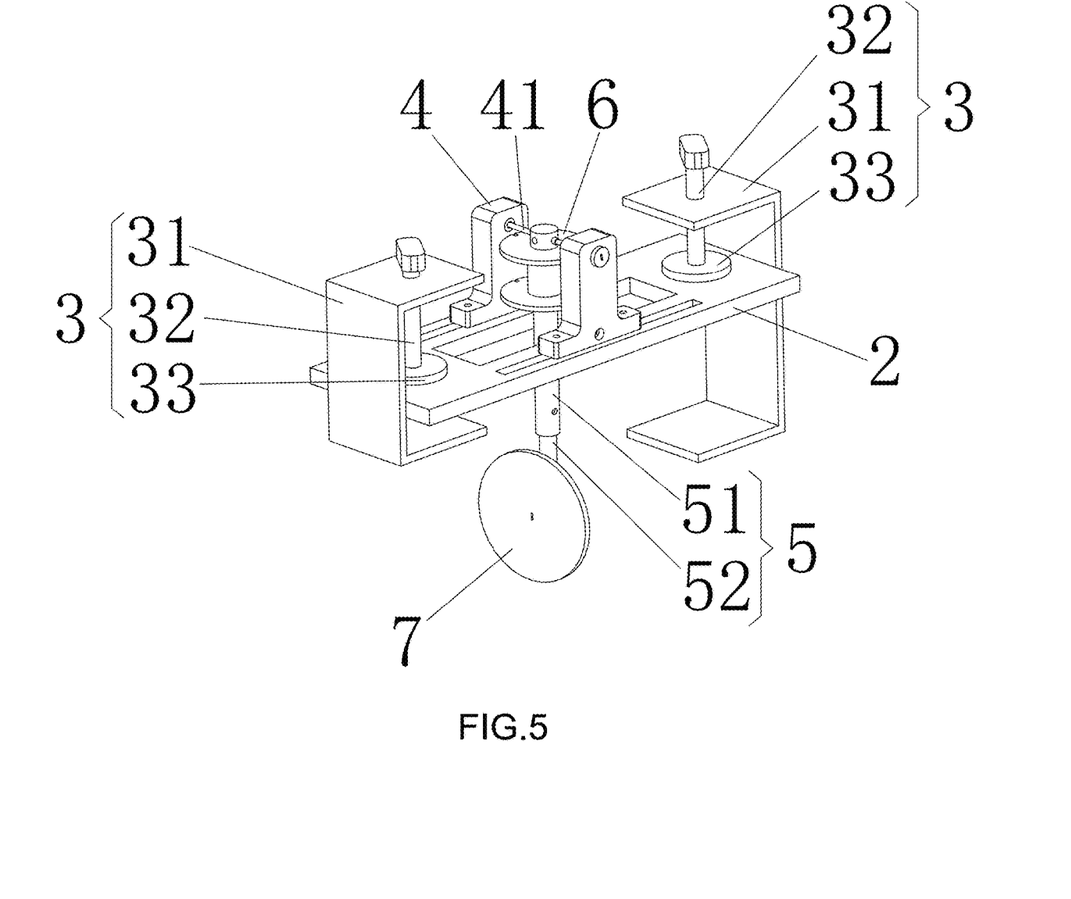
FIG. 5 is a schematic view of the magnetic resonance elastography actuator for brain tissue of the present invention.
Figure 6:
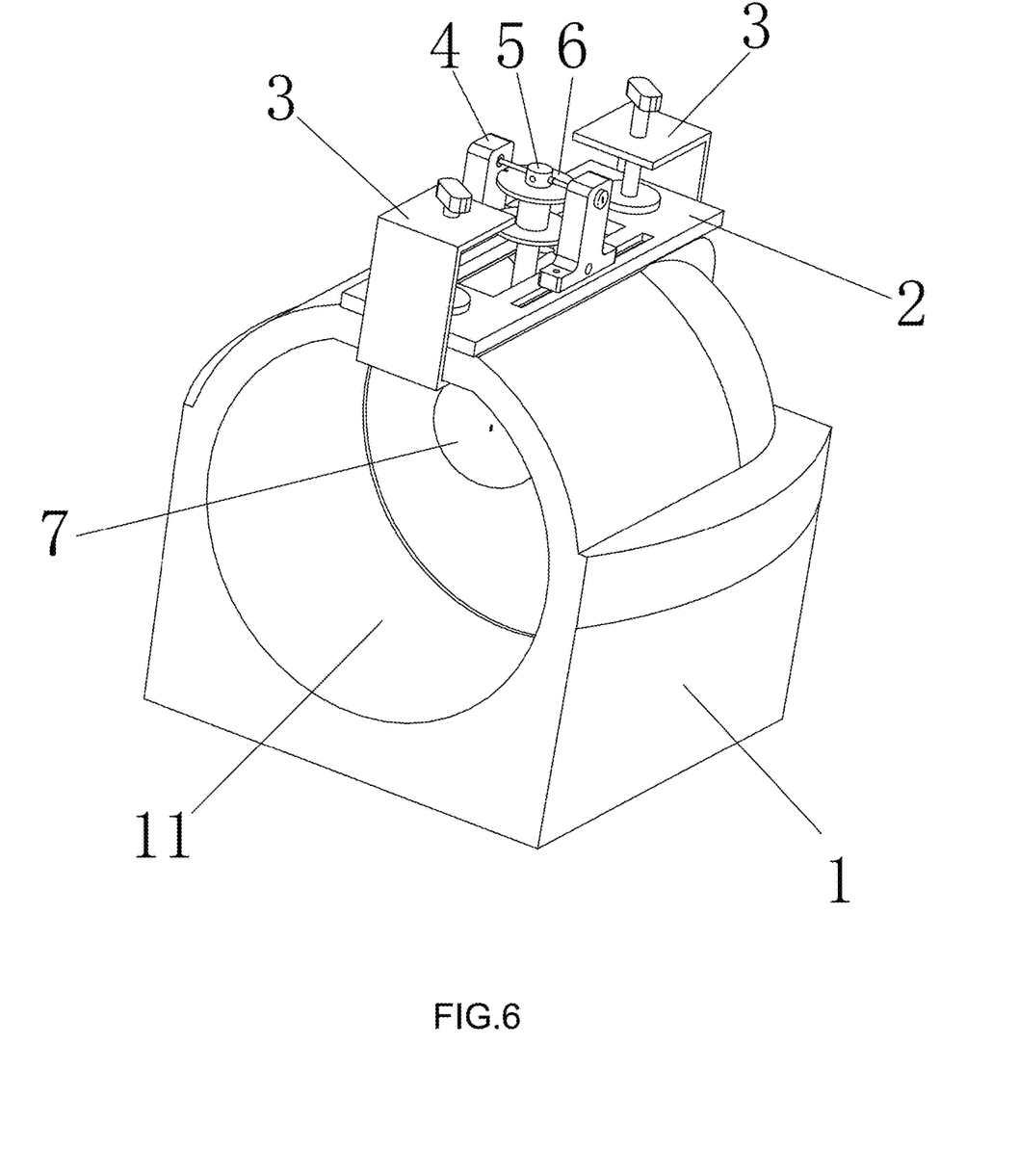
FIG. 6 is a schematic view of the actuator for brain tissue mounted on the head coil.
Figure 7:
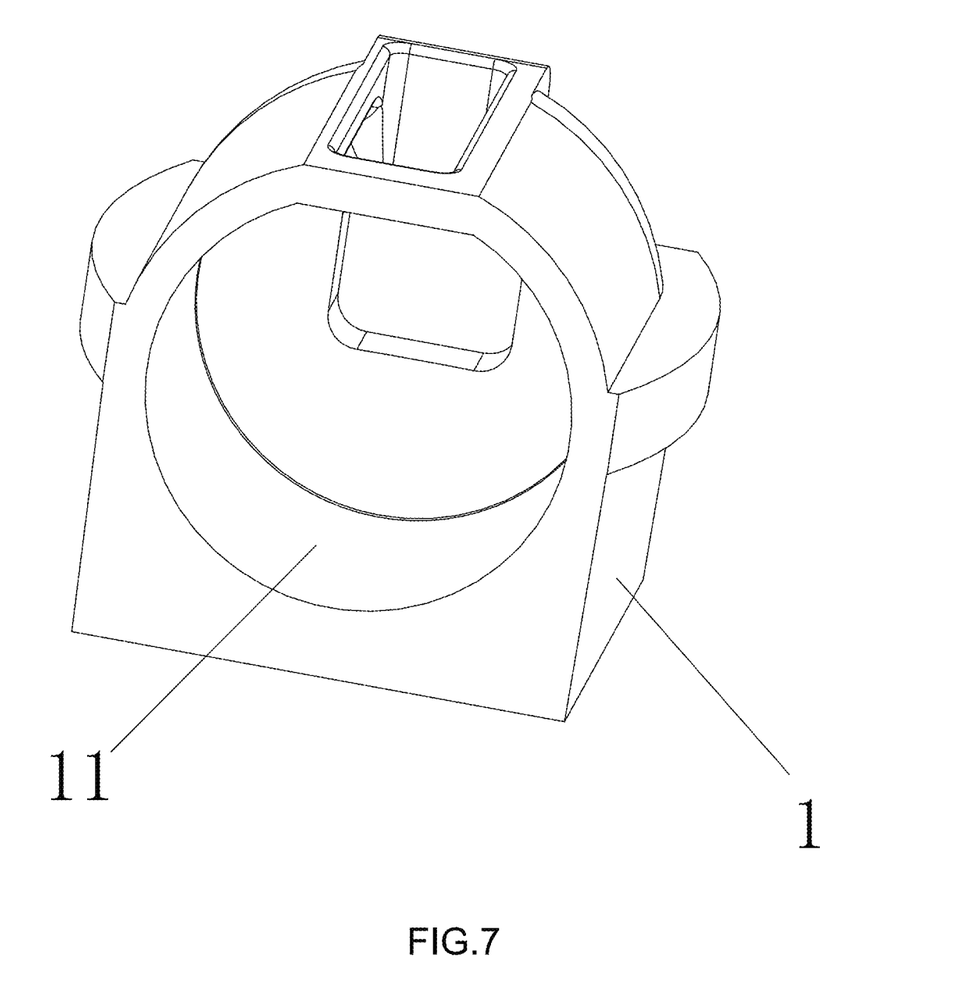
FIG. 7 is a schematic view of the head coil in FIG. 6.

A magnetic resonance elastography imaging apparatus for brain tissue, wherein the apparatus comprises the base 2 placed on top of the head coil 1; two clamps 3 for holding the base 2 on top of head coil 1; a positioning adjustment slider 4 that mounted on base 2, which can slide along the grooves of the base 2; a place holding device that can fix the position of slider 4 on top of base 2; a vibration plate 7 that connects to a supporting rod 5 mounted on the slider 4, placed at the end of the supporting rod 5. Both the head coil 1 and the base 2 have open grooves for allowing motions of the supporting rod 5. The end of the supporting rod 5 that connected to the vibration plate was placed inside of the head coil 1, in the open space of 11.

The supporting rod 5 comprises an upper part 51, a sliding hole is inside the upper part 51, a lower part 52 that can slide inside the sliding hole, and a locking part that can fix the relative position between the upper part 51 and lower part 52.

The adjustment slider 4 has a rotating shaft 41 on top, the supporting rod 5 is hinged to the rotating shaft 41. The axial direction of the rotating shaft 41 is perpendicular to the adjustment slider 4.

Clamps 3 comprises two U-shaped plates 31 that are arranged on both sides of the base 2 and are connected between the magnetic resonance head coil 1 and the base 2, two fixing bars 32 screwed on each of the U-shaped plates 31 respectively, and two compressing plates 33 at the ends of the fixing bars 32. When in a compressed state, the compressing plates 33 press on the upper surface of the base 2.

Embodiments (III)

Figure 8:
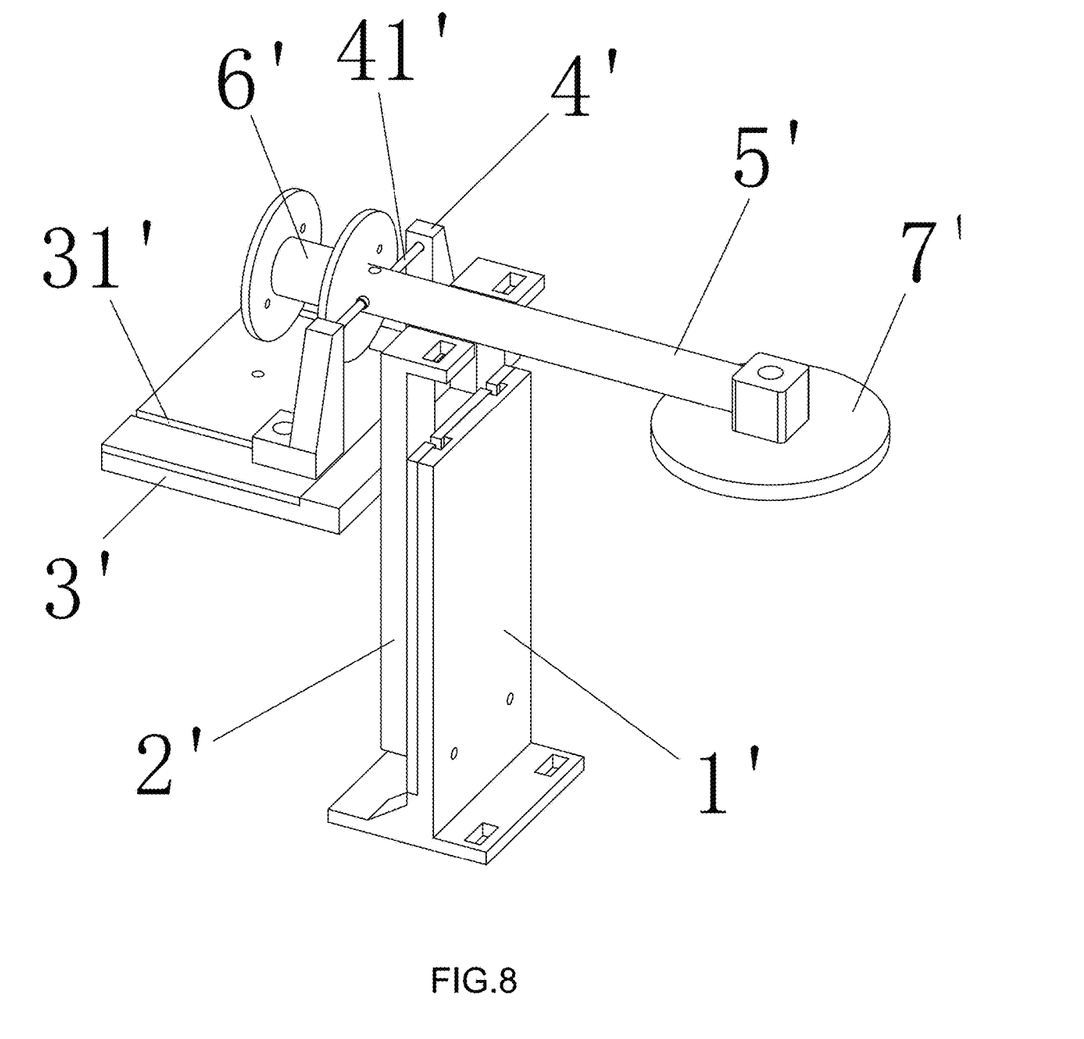
FIG. 8 is a schematic view of the magnetic resonance elastography actuator for abdomen region.

As shown in FIG. 8, an actuator for magnetic resonance elastography imaging of the abdomen region, wherein it comprises of a base 1', a lifting base 2' that is placed on the base 1' and can sliding relative to the base 1', a locking mechanism I placed between bases 1' and lifting base 2' for fixing the relative position of the base 2' and lifting base 2', a mounting base 3' that is installed on the side of the lifting base 2', a sliding base 4' installed on the mounting base 3' that can slide relative to the mounting base 3'. A locking mechanism II installed between the mounting base 3' and the sliding base 4' for limiting the motion between the sliding base 4' and the mounting base 3', and the supporting rod 5' hinged on the sliding base 4'. The actuator for magnetic resonance elastography imaging also includes a electromagnetic coil 6' installed on the supporting rod 5' that is closed to the mounting base 3', a compressing plate 7' installed at the end of the supporting rod 5'. The hinge axis of the supporting rod 5' is perpendicular to the axis of the supporting rod 5', and close to the coil 6'. The lifting base 2' has curved grooves on top for placing the supporting rod 5'.

The rotating shaft 41' is installed on top of the sliding base 4', the supporting rod 5' is hinged to the rotating shaft 41'.

The lifting base 2' connects to the base 1' via sliding block module, the locking mechanism I are threaded bolts between the lifting base 2' and base 1'.

The mounting base 3' has two parallel sliding grooves 31', the sliding base 4' has positioning block that matches the sliding grooves 31', the locking mechanism II are a threaded bolts between the mounting base 3' and the sliding base 4'.

Figure 9:
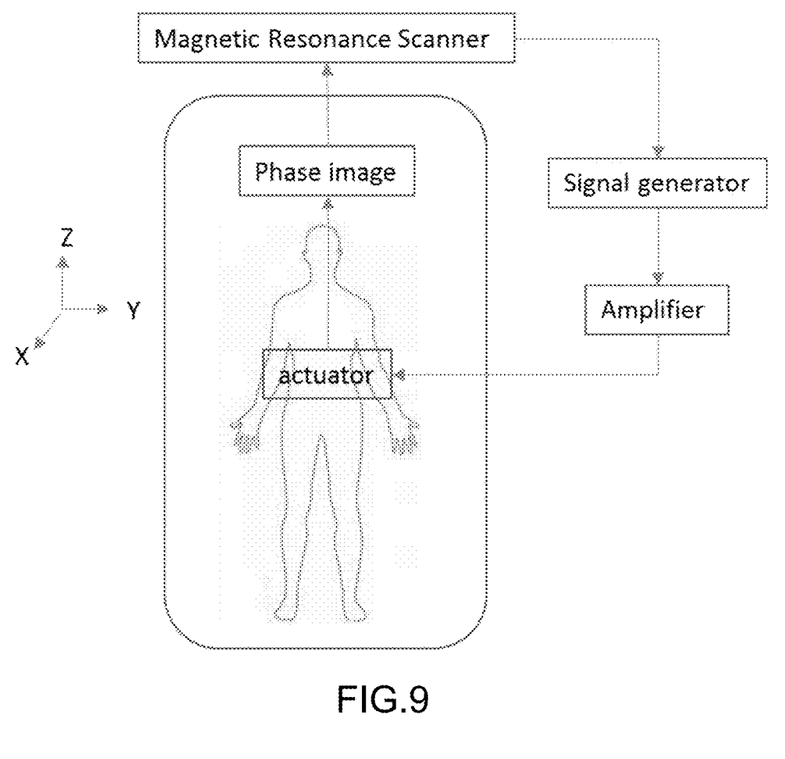
FIG. 9 is a schematic view of the implementation of the abdomen actuator in use.

When using the actuator for magnetic resonance elastography imaging of the abdomen region, first place the base 1' on top of the patient bench. An elastic belt is used to fix the actuator on the side of the patient. Adjust the position of the lifting base 2' relative to base 1', and adjust the position of sliding base 4' in the grooves of 31', so that compressing plate 7' is placed right on the desired examination position, then lock the positions using locking mechanism I and II. As shown in FIG. 9, connect the actuator coil 6' to an amplifier, and produce a sinusoidal signal with a frequency of ω using the signal generator. Adjust the amplifier output so that the vibration magnitude is amiable for the patient.

Figure 10:
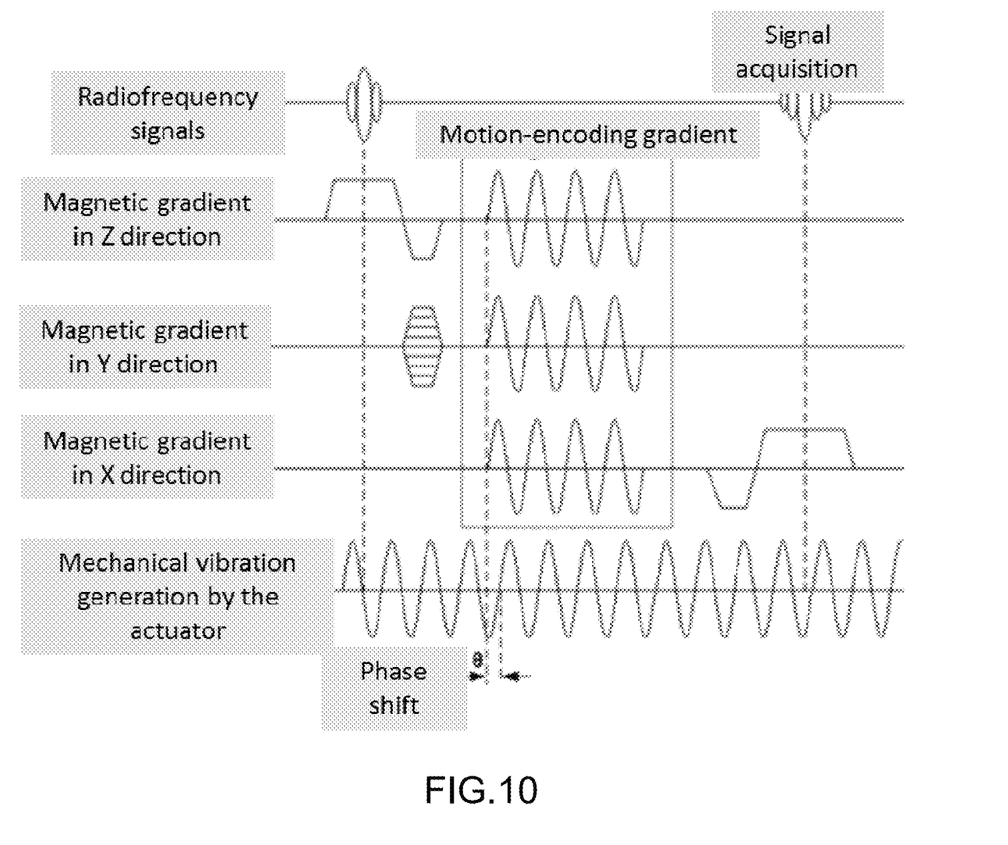
FIG. 10 is a sequence map of one magnetic resonance elastography.

As shown in FIG. 10, add motion-encoding gradient to imaging sequences such as gradient-echo sequence. The motion-encoding gradient can be either sinusoidal or trapezoidal. Set the frequency of the motion-encoding gradient to the same as the actuator vibration frequency, ω. The motion-encoding gradient can be applied to either X, Y, or Z direction of the gradient, for measuring the displacement in the designated direction. Produce the actuation signal from the signal generator, triggered by the sequence output from the magnetic resonance scanner. The signal is amplified and output to the actuator coil 6.

Take an example using the motion-encoding gradient $G_z$ in the Z direction. Add motion-encoding gradient with a frequency of ω in the Z direction. Set up the trigger signal so that the motion-encoding gradient $G_z$ has a phase shift θ of relative to the actuator frequency. Sample four temporal points $$\left(\theta = 0, \frac{\pi}{4}, \frac{\pi}{2}, \frac{3\pi}{4}\right)$$

for measurement, and acquire images at each temporal point. By combining the sampling information, the mechanical shear wave propagation in the soft tissue can be acquired base on the images.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:
1. An actuator for magnetic resonance elastography imaging of the abdomen region, consisting of:
   a base (1'),
   a lifting base (2') that is placed on the base (1') and adapted for sliding relative to the base (1'),
   a first locking mechanism placed between the base (1') and the lifting base (2') for fixing a relative position of the base (1') and the lifting base (2'),
   a mounting base (3') that is installed on a side of the lifting base (2'),
   a sliding base (4') installed on the mounting base (3') that is adapted for sliding relative to the mounting base (3'),
   a second locking mechanism installed between the mounting base (3') and the sliding base (4') for limiting the motion between the sliding base (4') and the mounting base (3'), and
   a supporting rod (5') hinged on the sliding base (4'),
   wherein a rotating shaft (41') is installed on top of the sliding base (4'), and the supporting rod (5') is hinged to the rotating shaft (41');
   wherein the actuator for magnetic resonance elastography imaging also includes an electromagnetic coil (6') installed on a first end of the supporting rod (5') that is connected to the sliding base (4'), a compressing plate (7') installed at a second end of the supporting rod (5'), a hinge axis of the supporting rod (5') is perpendicular to an axis of the supporting rod (5'), and the lifting base (2') has curved grooves on top for placing the supporting rod (5');
   wherein the hinge axis of the supporting rod (5') is an axis of the rotating shaft (41');
   wherein the lifting base (2') connects to the base (1') and the first locking mechanism includes threaded bolts between the lifting base (2') and base (1');
   wherein the mounting base (3') has two parallel sliding grooves (31'), the sliding base (4') has a positioning block that is adapted for engaging the sliding grooves (31'), and the second locking mechanism includes threaded bolts between the mounting base (3') and the sliding base (4');

wherein the electromagnetic coil (6') is connected to an amplifier, a sinusoidal signal with a frequency of $\omega$ is produced by using a signal generator, and an amplifier output is adjusted; and wherein the actuator is adjustable for the patients with different sizes and weights.

* * * * *